United States Patent
Wiesbeck

(10) Patent No.: US 9,434,790 B2
(45) Date of Patent: Sep. 6, 2016

(54) PROCESS FOR THE EXTRACTION OF WOOD

(75) Inventor: Franz Wiesbeck, Feusisberg (CH)

(73) Assignee: LDA AG, Wollerau (CH)

( * ) Notice: Subject to any disclaimer, the term of this patent is extended or adjusted under 35 U.S.C. 154(b) by 0 days.

(21) Appl. No.: 14/376,399

(22) PCT Filed: Feb. 2, 2012

(86) PCT No.: PCT/EP2012/000476
§ 371 (c)(1),
(2), (4) Date: Nov. 10, 2014

(87) PCT Pub. No.: WO2013/113331
PCT Pub. Date: Aug. 8, 2013

(65) Prior Publication Data
US 2015/0080566 A1     Mar. 19, 2015

(51) Int. Cl.
*B01D 11/02* (2006.01)
*B01D 11/00* (2006.01)
*C08B 37/00* (2006.01)
*C07D 311/62* (2006.01)
*C07D 311/40* (2006.01)

(52) U.S. Cl.
CPC ......... *C08B 37/006* (2013.01); *B01D 11/0219* (2013.01); *C07D 311/40* (2013.01); *C07D 311/62* (2013.01)

(58) Field of Classification Search
CPC ............. B01D 11/11; B01D 11/0215; B01D 11/0288
USPC .......................................... 530/202; 202/169
See application file for complete search history.

(56) References Cited

U.S. PATENT DOCUMENTS

| 1,762,785 | A |   | 6/1930  | Little |
|-----------|---|---|---------|--------|
| 3,171,872 | A | * | 3/1965  | Jarrett ...................... B27N 3/14 264/113 |
| 3,325,473 | A | * | 6/1967  | Herrick ................. C08B 37/006 536/127 |
| 3,944,677 | A |   | 3/1976  | Katz |
| 5,364,475 | A | * | 11/1994 | Levien ..................... D21C 1/00 134/19 |

FOREIGN PATENT DOCUMENTS

| CA | 1032826 A1   |   | 6/1978  |              |
| CN | 101532261 A  |   | 9/2009  |              |
| CN | 101591325 A  |   | 12/2009 |              |
| DE | 4206795 A1   | * | 2/1994  | ........... C05F 17/009 |

OTHER PUBLICATIONS

International Search Report and Written Opinion dated Nov. 19, 2012 for Application No. PCT/EP2012/000476.

* cited by examiner

*Primary Examiner* — Patrick Lewis
*Assistant Examiner* — Everett White
(74) *Attorney, Agent, or Firm* — Patterson & Sheridan, LLP

(57) ABSTRACT

The invention relates to a process for the extraction of wood, comprising the following steps: providing wood particles, at least a first class and a second class, stacking a fine layer consisting of the first class wood particles over a further layer consisting of the second class wood particles, and extracting the wood particles using a liquid extractant, in which the extractant flows from the top downwards, first through the fine layer and then through the further layer, in which the wood particles of the first class are finer than the wood particles of the second class, and thus the fine layer has a lower permeability than the further layer.

12 Claims, 2 Drawing Sheets

PROCESS FOR THE EXTRACTION OF WOOD

This invention relates to a process for the extraction of wood. In particular, taxifolin and/or arabinogalactan are/is extracted from wood.

Wood is usually chopped or chipped before extraction. The resulting wood chips and/or the chipped product are/is filled in a percolator and the appropriate extraction fluid introduced.

It is the object of the present invention to provide a process for the extraction of wood which, with a cheaper and more reliable implementation, enables a rapid, high-yielding and energy-efficient extraction of the respective substances from the wood in question. In particular, with the use of ethanol, taxifolin should be extracted as efficiently as possible from the wood, and/or with the use of water arabinogalactan should be extracted as efficiently as possible from the wood.

The problem is solved by the features of claim 1. The object of dependent claims is the preferred embodiments according to the invention.

Thus, the object is achieved by a process for the extraction from wood, comprising the following steps:
(i) providing wood particles, at least a first class and a second class
(ii) stacking a fine layer consisting of the first class wood particles on a further layer that consists of the second class wood particles
(iii) extracting the wood particles with a liquid extractant (also: extraction fluid, or solvent), wherein the extractant first flows from top to bottom through the fine layer and then through the further layer. According to the invention, the wood particles of the two classes differ in their fineness. The wood particles of the first class are finer than the wood particles of the second class. Thus, the fine layer possesses a lower permeability than the further layer. The "permeability" of a layer describes the amount of extractant that runs through the layer, with the same layer thickness, at the same pressure and at the same time. To compare the permeability of different layers, the flow rate of extractant must be measured through layers with the same layer thickness, at the same pressure and at the same time. A lower flow rate means a lower permeability of the respective layer. Alternatively, the "permeability" of different layers can also be measured at a constant flow rate and variable pressure. If a higher pressure for the same flow rate is required, then the layer is considered to have a lower permeability. When carrying out the process according to the invention, the individual layers are preferably arranged as horizontal layers in a percolator. In this case, the extractant is introduced from the top of the percolator. The fine layer is arranged such that the extraction fluid is forced to flow first through the fine layer and then through the further layer comprising the wood particles of the second class. The lower permeability of the fine layer thus increases the pressure above the fine layer and reduces a pressure drop along the height of the layers. This improves the circulation capability of the extractant.

Very small wood particles, in particular less than 1 mm, are not desirable from a procedural point of view because of their poor permeability, but cannot be avoided during the comminution. The main advantage of the fine layer according to the invention is that it prevents an excessive pressure drop during the extraction. In particular, the fine layer reduces a pressure drop above the percolator bed, which improves the circulation capability of the liquid extractant. The liquid extractant passes through the percolator in particular in several cycles. With each pass the extractant passes through the fine layer, so that the fine wood particles and any impurities remain caught in the fine layer. As a result, the extractant that is ultimately drained from the percolator is as free as possible from fine wood particles and impurities. Preferably, the extractant no longer needs to be filtered after leaving the percolator or process according to the invention significantly reduces the service life and/or the dimension of the filter unit that is downstream of the percolator. The fine layer thus also serves as a prefilter.

Figure 1:
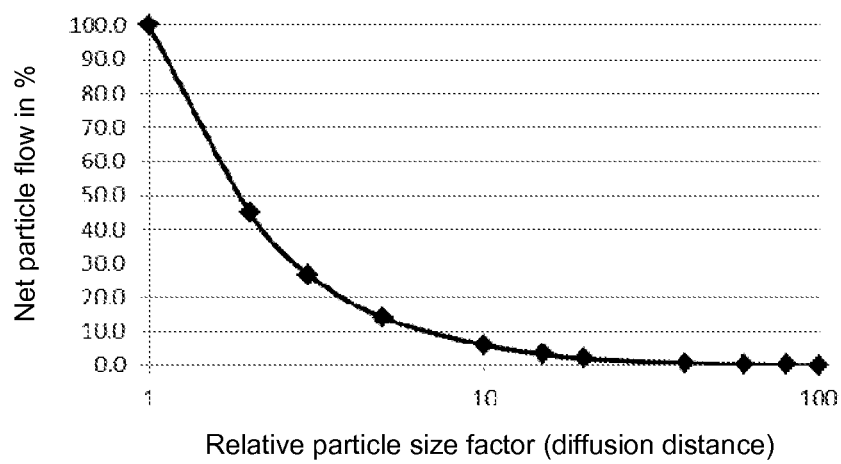
FIG. 1 is a graph illustrating theoretical net particle flow as a function of the particle size.

In a preferred embodiment, differentiation is made between fine and coarse wood particles by means of the median value of the particle size distribution. Thus, it is preferable if the median value (first median value) of the particle size distribution of all wood particles in the first class is lower than the median value (second median value) of the particle size distribution of all wood particles in the second class.

The particle size is, in particular, the nominal screen size of the wood particle. The nominal screen size of the wood particle is the hole size of a screen through which at least a mass fraction of 95% of the material still passes.

Particularly preferred for the determination of the nominal screen size is to involve a screening process according to DIN EN 15149-1: 2010 and/or DIN EN 15149-2: 2010. According to these standards, an appropriate number of stacked screens must be used to determine the nominal screen size and the corresponding size distribution. In this case, the hole diameter and/or the mesh size of individual screens decreases from top to bottom. A horizontal one- or two-dimensional vibration of the screen pack takes place. Further, these two standards also define the median value of the particle size distribution. Accordingly, the median value is the value that divides a distribution in two equal parts and graphically represents the intersection of the cumulative size distribution curve with the 50% horizontal line. Wood particles with a smaller median value of particle size distribution are preferred to "finer wood particles" and are thus used for the fine layer.

Particularly preferred is for the median value (first median value) in the first class to be less than or equal to 3 mm, preferably less than or equal to 2 mm, particularly preferably less than or equal to 1 mm, more particularly preferably less than or equal to 0.5 mm. The smaller the median value in the first class, the slower the solvent flows through the fine layer. Thus, the pressure drop can be adjusted by selecting the median value and the height of the fine layer.

Preferably the process also comprises the following steps: to provide the wood particles, wood is initially crushed into wood particles of various sizes. The comminution is carried out by chopping and/or shredding and/or grinding. The shredded or chopped or ground wood is then classified. The classification is carried out in particular by screening. The classification makes a distinction between at least wood particles of the first class and wood particles of the second class. It is essential in the classification that sufficiently fine wood particles of the first class are separated. It is not necessary for all the fine wood particles to be separated from the second class.

In addition to the classification of the chopping or shredding or grinding material, sawdust and/or shavings produced otherwise can be added to the first class. Furthermore, as an alternative to the classification it is also possible that the fine layer is only formed from sawdust and/or wood shavings and/or wood dust that has/have been processed otherwise.

In a particularly preferred embodiment it is provided that for classification of the first class and the second class, a screen having a certain mesh size or a specific hole diameter is used. The screen size or the hole diameter preferably lie between 0.5 mm and 7 mm. The experiment has shown that it is possible to implement a practical separation between the two classes in particular with a mesh size or a hole diameter from 1 mm and 6 mm, preferably between 1 mm and 4 mm. Depending on water and resin content and the nature of the comminution of wood, the unclassified material has different characteristics regarding the particle size distributions. Accordingly, a screening of the first class is achieved here with the preferred mesh sizes or hole diameters.

Further, a differentiation can be made between fine and coarse wood particles based on the amount of oversized wood particles in the classes. It is advantageous if not too many oversize wood particles exist in the fine layer. This ensures that the permeability over the entire fine layer is constant. Therefore, it is preferably provided that more than 70% mass fraction of the wood particles in the first class have a nominal screen size of 4 mm, preferably 2 mm, particularly preferably 1 mm. During comminution of the wood, the amount of wood particles of the first class, for example, depends on the water and resin content as well as on the applied comminution technique. Thus, the size distribution of the wood particles during comminution cannot be set arbitrarily.

It is advantageous that the extractant runs relatively defined and unimpeded through the further layer. This is why the second class should have as few as possible fine wood particles. It is preferably provided that more than 30% mass fraction of the wood particles in the second class have at least a nominal screen size of 2 mm, preferably 3 mm.

Furthermore, it is preferred that the degree of fineness of the wood particles in the fine layer is sufficiently low, and that as few as possible large and oversize wood particles are present. Therefore, an upper limit is defined for the nominal screen size of wood particles of over 60%, preferably over 70%, particularly preferably over 80% mass fraction of all wood particles that are in the first class. In the further layer there should be a sufficiently large amount of wood particles present in order to ensure a defined and adequate flow of the extractant. A lower limit is defined for the nominal screen size of the wood particles of over 10%, preferably over 20%, particularly preferably over 30% mass fraction of all wood particles of the second class. Preferably it is provided that the upper limit of the first class is equal to or less than the lower limit of the second class. Particularly preferably, the upper limit of the first class is 4 mm, preferably 2 mm, most preferably 1 mm.

Depending on the nature of the chopped, chipped or ground wood, more or less material of the first class is produced. Preferably, a layer height of the fine layer is specified. First, the fine layer should not be too high to ensure a sufficient flow of the extractant. On the other hand, a certain height of the fine layer is necessary to obtain a sufficient filtration effect and to avoid too great a pressure drop. It has proven advantageous to have a fine layer height of 5% to 70%, preferably 5% to 50%, particularly preferably of 5% to 40% based on the total height of all layers.

Preferably, the wood particles are stacked up in a percolator. The process according to the invention is preferably used in the extraction of large quantities. The fine layer height in this case is advantageously 0.5 m, preferably 1 to 3 m.

Preferably an extraction of larch wood is carried out. It is particularly preferable to use only the heartwood trunk and/or the root stock of the larch.

Furthermore, with the process according to the invention, in particular an extraction of taxifolin from wood is carried out using an organic solvent, preferably ethanol. Additionally or alternatively, an extraction of arabinogalactan from wood takes place preferably using water as the solvent.

The sampling from the chipped or chopped or ground wood is preferably carried out according to DIN EN 14778: 2011 and the determination of the size of wood particles and the particle size distribution according to DIN EN 15149-1: 2010 and/or DIN EN 15149-2: 2010.

Several fine layers or several further layers can be stacked as required.

The extraction is theoretically based on Fick's diffusion laws. From this, it can be inferred on the one hand that the shorter the required diffusion distance from the extraction material is in the solvent, the faster the desired product can be extracted from the extraction material. From this it can be concluded that the smaller the particles of the extraction material used, the lower the diffusion distance to be overcome is, and thus the greater the theoretical net particle flow into the solvent. FIG. 1 shows a characteristic of the theoretical net particle flow depending on the particle size.

On the other hand, it can be deduced that the greater the concentration gradient of the product concentration in the particle to the solvent is, the quicker the desired product can be extracted from the extraction material.

Figure 2:
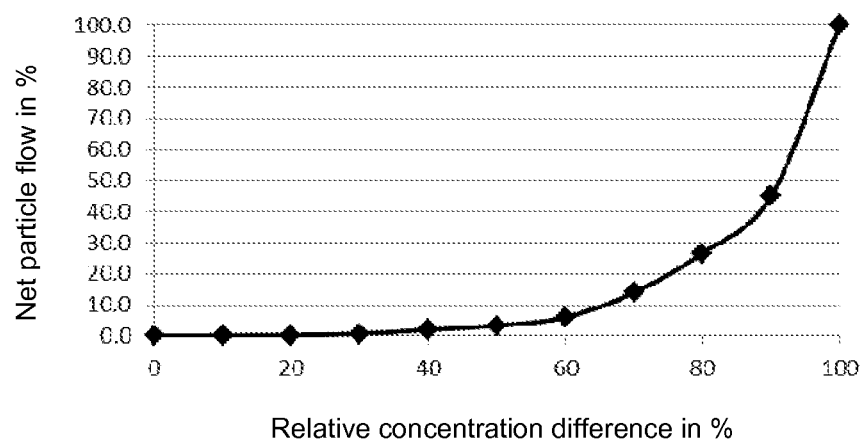
FIG. 2 is a graph illustrating theoretical net particle flow as a function of the concentration gradient.

From this, it can be concluded that the higher the circulation rate or the amount of the solvent used, the greater the concentration gradient driving the diffusion and thus the greater the theoretical net particle flow in the solvent. FIG. 2 shows a characteristic of the theoretical net particle flow as a function of the concentration gradient.

Figure 3:
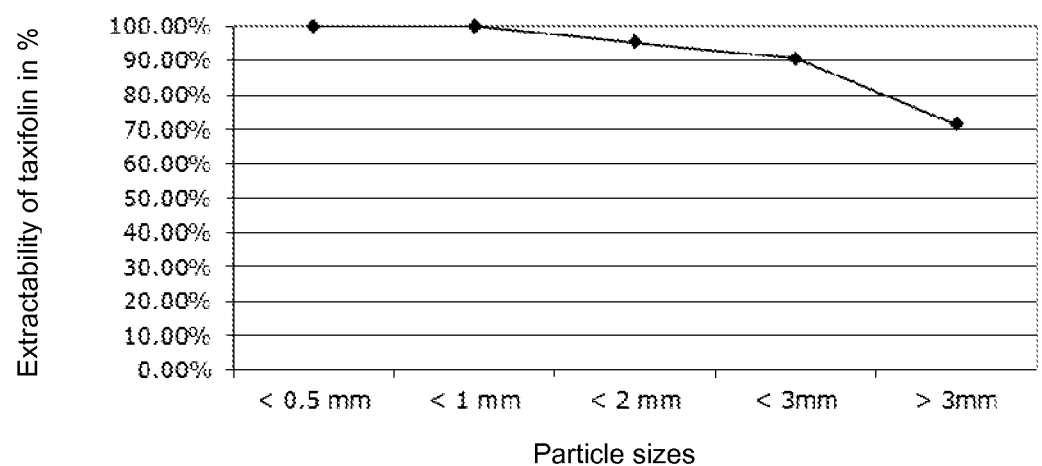
FIG. 3 is a graph illustrating extractability of taxofolin from wood as a function of particle size.

A series of experiments was carried out on the extractability of taxifolin from larch wood as a function of the particle sizes used. The extraction times, extraction temperature, mixing, and the ratio of solvent relative to extraction material was kept constant in this case. FIG. 3 shows the course of the extractability of taxifolin from larch wood as a function of the nominal screen size of the wood particles.

The invention claimed is:

1. A process for the extraction of wood, comprising:
   providing wood particles including at least a first class and a second class,
   stacking a fine layer consisting of the first class wood particles on a further layer consisting of the second class wood particles, and
   extracting the wood particles using a fluid extractant in which the extractant flows from top downwards initially through the fine layer and subsequently through the further layer,
   wherein the wood particles of the first class are finer than the wood particles of the second class, and thus the fine layer has a lower permeability than the further layer.

2. The process according to claim 1, wherein a first median value of the particle size distribution of all the wood particles in the first class is lower than a second median value of the particle size distribution of all the wood particles in the second class, in which particularly the particle size is the nominal screen size.

3. The process according to claim 2, wherein the first median value is less than or equal to 3 mm.

4. The process according to claim 1, wherein the provision of wood particles comprises:
   comminuting wood into wood particles of various sizes, and
   classifying, particularly screening the wood particles into at least the first class and the second class.

5. The process according to claim 4, wherein a classification is made for the first class and the second class by using a mesh size or hole diameter between 0.5 mm and 7 mm.

6. The process according to claim 1, wherein over 70% mass fraction of the wood particles in the first class has a nominal screen size of at most 4 mm.

7. The process according to claim 1, wherein over 30% mass fraction of the wood particles in the second class has a nominal screen size of at least 2 mm.

8. The process according to claim 1, wherein the nominal screen size of the wood particles of over 60% mass fraction of all the wood particles in the first class is less than or equal to a first limit value, and that the nominal screen size of the wood particles of over 10 mass fraction of all wood particles of the second class is greater than or equal to a second limit value, in which the first limit value is equal to or less than the second limit value.

9. The process according to claim 8, wherein the first limit value has a nominal screen size of 4 mm.

10. The process according to claim 1, wherein a layer height of the fine layer is 5% to 70% of a total height of all layers.

11. The process according to claim 1, wherein the wood particles are stacked in a percolator, in which the height of the fine layer is at least 0.5 m.

12. The process according to claim 1, wherein at least one of taxifolin is extracted from wood with ethanol as extractant or arabinogalactan is extracted from wood using water as extractant.

* * * * *